United States Patent
Hsu

(10) Patent No.: US 9,498,412 B2
(45) Date of Patent: Nov. 22, 2016

(54) METHOD FOR PRODUCING MICROCAPSULES WITH A SUN PROTECTION EFFECT

(71) Applicant: Greenjoy Biotech Co., Ltd., Taichung (TW)

(72) Inventor: Jaw-Cherng Hsu, Taichung (TW)

(73) Assignee: Greenjoy Biotech Co., Ltd., Taichung (TW)

( * ) Notice: Subject to any disclaimer, the term of this patent is extended or adjusted under 35 U.S.C. 154(b) by 232 days.

(21) Appl. No.: 14/310,382

(22) Filed: Jun. 20, 2014

(65) Prior Publication Data

US 2015/0023894 A1  Jan. 22, 2015

(51) Int. Cl.
- *A61K 8/11* (2006.01)
- *A61Q 17/04* (2006.01)
- *A61K 8/891* (2006.01)
- *A61K 8/34* (2006.01)
- *A61K 8/49* (2006.01)

(52) U.S. Cl.
CPC . *A61K 8/11* (2013.01); *A61K 8/34* (2013.01); *A61K 8/4973* (2013.01); *A61K 8/891* (2013.01); *A61Q 17/04* (2013.01); *A61K 2800/82* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 6,607,713 B1 * | 8/2003 | Chodorowski | A61K 8/042 424/401 |
| 2002/0037261 A1 * | 3/2002 | Lapidot | A61K 8/042 424/59 |
| 2004/0057918 A1 * | 3/2004 | Chodorowski-Kimmes | A61K 8/042 424/59 |
| 2008/0199526 A1 * | 8/2008 | Poschalko | A61K 8/11 424/490 |

OTHER PUBLICATIONS

A Jaroenworaluck, W Sunsaneeyametha, N Kosachan, R Stevens. "Characteristics of silica-coated TiO2 and its UV absorption for sunscreen cosmetic applications." Surface and Interface Analysis, vol. 38, 2006, pp. 473-477.*

* cited by examiner

*Primary Examiner* — Isaac Shomer
(74) *Attorney, Agent, or Firm* — Alan D. Kamrath; Kamrath IP Lawfirm, P.A.

(57) ABSTRACT

A method for producing microcapsules with a sun protection effect includes mixing tetraethoxysilane (TEOS), ethanol, and water and uniformly vibrating the mixture of TEOS, ethanol, and water. The TEOS, ethanol, and water have an appropriate ratio therebetween. Nitric acid is used to adjust the mixture of TEOS, ethanol, and water to have an appropriate pH value. The mixture is placed still to hydrolyze the mixture. The hydrolyzed mixture is heated and stirred to obtain a TEOS sol. Then, the TEOS sol, Span 80, and mineral oil are mixed in an approximate ratio to obtain a microemulsified TEOS gel. The microemulsified TEOS gel is centrifuged. The upper oil phase is removed. The lower water phase and powders are sucked, filtered, and cleaned. The powders are recycled and baked.

9 Claims, 8 Drawing Sheets

METHOD FOR PRODUCING MICROCAPSULES WITH A SUN PROTECTION EFFECT

BACKGROUND OF THE INVENTION

The present invention relates to a method for producing a microcapsule with a sun protection effect and, more particularly, to a method using silica to produce microcapsules with micromized diameters to significantly increase the sun protection effect when applied to a skin of a user.

Ultraviolet (UV) rays can cause serious injury to the skin, including swelling, sunburn, pigmentation, aging, loosing elasticity, and wrinkles, and can even damage the skin immune system and increase the chance of getting skin cancer. The destruction to the environment aggravates the invasion of ultraviolet rays. Thus, sun protection should not be ignored.

Although UV filters can resist ultraviolet rays, the side effects, including irritation to the skin, inflammation of the skin, skin sensitization, and phototoxic reaction, are undesirable. Thus, it is desirable to research and develop effective sun protection products with minimal side effects to the skin while reducing the burden to the environment. Chemical UV filters achieve the sun protection effect through energy transfer. However, photodegradation occurs in some of the UV filters due to the energy provided by the ultraviolet rays, producing harmful free radicals and phototoxic substances while reducing the sun protection effect.

A silica microcapsule formed by a sol-gel/emulsion technique can provide a sun protection effect as physical UV filters. When used together with a chemical UV filter, the silica microcapsule can reduce the quantity demand of the chemical UV filter. The chemical UV filter can be entrapped by the silica microcapsule to avoid photodegradation and phototoxicity while avoiding direct contact with the skin to avoid allergic reaction.

BRIEF SUMMARY OF THE INVENTION

A method for producing microcapsules with a sun protection effect according to the present invention includes:

hydrolysis and condensation: mixing tetraethoxysilane (TEOS), ethanol, and water in an appropriate ratio and uniformly vibrating the mixture, and an appropriate pH value will be adjusted by nitric acid, heating and stirring the hydrolyzed mixture to obtain a TEOS sol; and microemulsion polymerization: mixing the TEOS sol, Span 80, and mineral oil in an approximate ratio to obtain a mieroemulsified TEOS gel. After polymerization, centrifuging the mieroemulsified TEOS gel and removing the upper oil phase, filtering the lower water phase with powders, and baking the powders in an oven.

Preferably, the ratio of TEOS, ethanol, and water is 1:1-5:2-10.

Preferably, the pH value of the mixture of TEOS, ethanol, and water is 0-4.

Preferably, in the hydrolysis and condensation, the supersonic vibration is carried out for 5-40 minutes, the heating temperature is 50-95° C., the stirring speed is 500-3000 rpm, and the stirring time is 20-120 minutes.

Preferably, the ratio between TEOS sol, Span 80, and mineral oil is 1:0.5-4: 1-10.

Preferably, in the microemulsion polymerization, the heating temperature is 50-95° C., the stirring speed is 500-3000 rpm, the stirring time is 20-120 minutes, the centrifuging speed is 3000-7000 rpm, the centrifuging time is 10-50 minutes, the oven temperature is 35-80° C., and the baking time is 8-36 hours.

Preferably, a UV filter is added in the hydrolysis and condensation, and the UV filter, TEOS, and ethanol are added in an appropriate ratio before mixing with water.

Preferably, the ratio between the UV filter, TEOS, and ethanol is 1:0.5-4: 1-10.

The present invention will become clearer in light of the following detailed description of illustrative embodiments of this invention described in connection with the drawings.

DETAILED DESCRIPTION OF THE INVENTION

Figure 1:
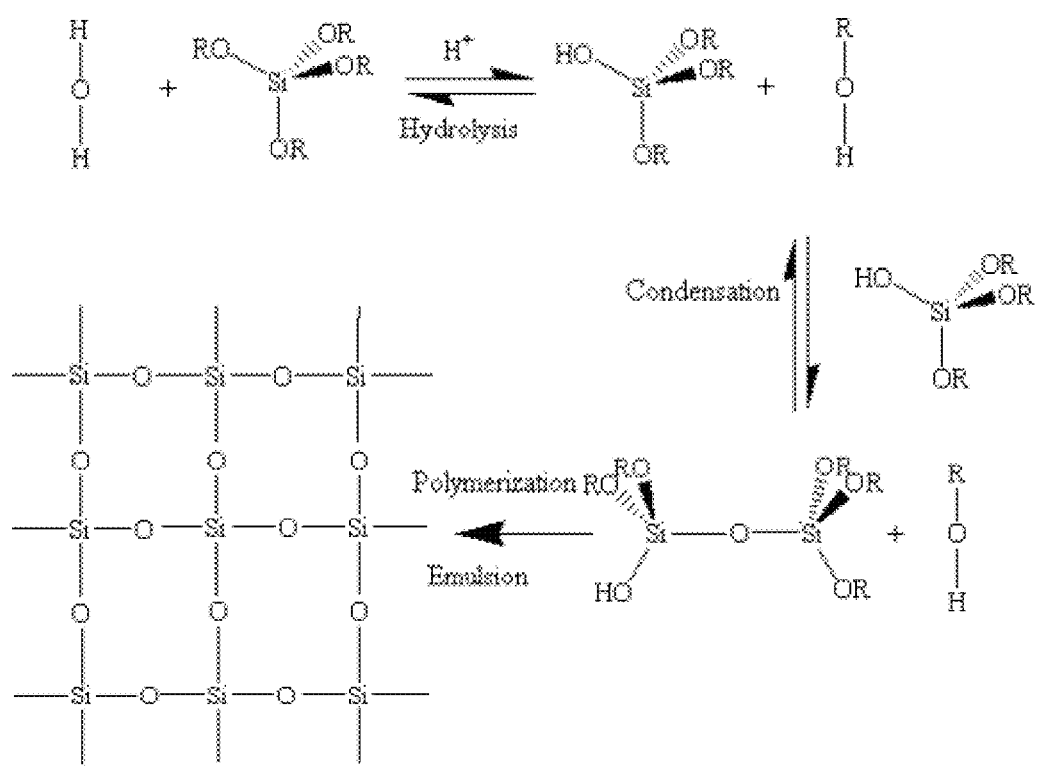
FIG. 1 is a diagrammatic reaction flowchart illustrating production of microcapsules by a sol-gel/emulsion technique.

FIG. 1 is a diagrammatic reaction flowchart illustrating production of microcapsules by a sol-gel/emulsion technique according to the present invention. A first embodiment of the present invention includes production of silica microcapsules (SMC). The first embodiment includes hydrolysis and condensation as well as microemulsion polymerization.

In hydrolysis and condensation, tetraethoxysilane (TEOS) and ethanol were mixed in a ratio of 1:3 (10 g of TEOS was dissolved in 30 g of ethanol), and the mixture of TEOS and ethanol was sonicated for 5-30 minutes by supersonic waves. Then, pure water was added into the mixture, such that TEOS, ethanol, and pure water were in the ratio of 1:1-5:2-10 (e.g., the solution included 10 g of TEOS 10 g, 30 g of ethanol 30 g, and 40 g of pure water 40 g), and the solution was sonicated for 5-30 minutes. Next, the pH value of the solution was adjusted to a range of 0-4 by using nitric acid (nitric acid 10N in this example). Then, the solution was placed still until the hydrolysis was completed, and the solution became clear.

The solution was then heated and stirred by a machine. In this example, the solution was heated at a heating temperature of 50-90° C. and stirred for 20-120 minutes at a speed of 50-300 rpm, obtaining a TEOS sol.

In microemulsion polymerization, the TEOS sol, Span 80 (sorbitane monooleate) and mineral oil were mixed at an appropriate ratio and were heated and stirred to obtain microemulsified TEOS (gel). The ratio between TEOS sol, Span 80, and mineral oil could be 1:0.5-4:10. In this example, 38.7 g of mineral oil and 10 g of Span 80 were uniformly mixed, and 10 g of TEOS sol was added. The mixture of TEOS sol, Span 80, and mineral oil were heated at a temperature of 50-95° C. and stirred for 20-120 minutes at a speed of 50-300 rpm, obtaining a TEOS gel.

The microemulsified TEOS gel was centrifuged, and, then, the upper oil phase was removed. In this example, the microemulsified TEOS gel was centrifuged for 10-50 minutes at a speed of 3000-7000 rpm. The lower water phase and powders were sucked and filtered and were cleaned twice by an organic solvent. The powders were collected and placed in an oven and dried for 8-36 hours at a temperature of 35-80° C., obtaining silica microcapsules (SMC).

A second embodiment of the present invention was a process for producing a single chemical UV filter/silica microcapsule, which is substantially the same as the first embodiment except the following. Specifically, in hydrolysis and condensation, a UV filter was dissolved in ethanol. The UV filter was a chemical UV filter, such as octyl methoxycinnamate (OMC, an UVB filter) or avobenzone (an UVA filter). After sonication for 10 minutes, TEOS was added into the UV filter. The ratio between the UV filter, TEOS, and ethanol was 1:0.5-4:1-10. In examples, the weight of the UV filter was 5 g, 10 g, and 15 g, respectively. The weights of TEOS and ethanol were 10 g and 30 g, respectively. Nitric acid was added to adjust the pH value to be in a range of 0-4.

In microemulsion polymerization, mineral oil, Span 80 and TEOS sol were mixed at an appropriate ratio and reacted to obtain microemulsified TEOS (gel). In the examples, the weights of mineral oil, Span 80, and TEOS sol were 38.7 g, 10 g, and 10.625-11.875 g, respectively.

In the examples, the silica microcapsules (SMC) produced from OMC were referred to as "O-SMC", and the silica microcapsules (SMC) produced from avobenzone were referred to as "A-SMC".

A third embodiment of the present invention was a process for producing a chemical UV filter complex/silica microcapsule, which is substantially the same as the second embodiment except the followings. In hydrolysis and condensation, a plurality of UV filters was mixed at an appropriate ratio to obtain a formula. The ratio of the UV filters for producing the chemical UV filter complex/silica microcapsule was decided by the sun protection abilities in the formula. In this embodiment, the UV filters were uniformly mixed with ethanol and TEOS in the hydrolysis stage at the ratio shown in Table 1.

TABLE 1

Preparation Ratio of OAB & OATD

|  | preparation ratio of OAB | preparation ratio of OATD |
| --- | --- | --- |
| OMC | 5 | 5 |
| avobenzone | 3 | 3 |
| BP-3 | 2 | — |
| Tinosorb M | — | 1 |
| DHHB | — | 1 |
| ethanol | 30 | 30 |
| TEOS | 10 | 10 |

The microcapsules were analyzed by the following analysis.

1. Particle Size Analysis: A laser particle size analyzer (such as Zetasizer Nano-ZS manufactured by Malvern Instruments Ltd., U.K.) capable of measuring particle sizes ranging between 6-6000 nm was used to measure the average diameter and polydispersity index (PDI value). A 10% sodium laureth sulfate (SLES) solution was prepared. Powders of 0.01 g were dispersed in 50 mL 10% SLES solution. The laser particle size analyzer was used to measure the particle size distribution. 5 ml solution was dipped into each cell, and each sample was measured three times to obtain the average value. The assessment parameters were the average particle size and the polydispersity index.

Suspension particles in the suspension solution were impacted by the liquid molecules and caused Brownian motion. The suspension particles changed the motion direction upon each impact. By using the change in the scattering light intensity of the suspension particles, the relevant time can be calculated based on the Stoke-Einstein Diffusion Coefficient Equation.

$$D = kBT/3\pi\eta d$$

wherein kB is Boltzmann constant ($1.38 \times 10^{-16}$ erg/K), T is temperature (K), $\eta$ is the viscosity of the diluted solution (poise, 1 poise=1 g/cm·s=100 cp), and d is the equivalent diameter of the particle (cm).

The diffusion coefficient of the suspension particles was obtained to analyze the diameters of the particles for calculating the polydispersity index (PDI) that represents the particle size distribution range. If the polydispersity index is closer to zero, the particle sizes are more uniform. If the polydispersity index is in a range of 0-0.3, the particle size distribution range is very small. If the polydispersity index is larger than 0.3, the particle size distribution range is wider.

2. Yield Rate Analysis:

Yield rate=weight of product/weight of reactants added during preparation×100%

3. Entrapment Efficiency (EE %): A high-performance liquid chromatography system was used to quantitatively analyze the entrapment efficiency. The injected volume was 50 µL. The detection wavelength was 310 nm. A mixture of 88% methanol, 11% water, and 1% acetic acid was used as the mobile phase with isocractic elution. The flow rate of the mobile phase was 1.0 mL/min. 1-100 ppm OMC and avobenzone standard solutions were used to create a calibration curve. Each concentration was detected three times to obtain the average value. Peak-ABC Chromatography Data Handling System (manufactured by Great Tide Instruments, Taiwan) was used to capture and handle the signals.

EE %=(total amount of drug−unentrapped drug)/total amount of drug×100%

4. Capacity (C %): The amount of the UV filter in SMC can be calculated from the above equation. The capacity can be obtained by the following equation:

C %=(total amount of drug−unentrapped drug)/ weight of product×100%

5. In Vitro Transdermal Delivery Analysis:

(1) Preparing penetration membranes from a swine skin: An ear skin of a 6-month-old Landrace pig was prepared and cleaned with deionized water. The upper skin of the pig ear was cut by a scalpel to remove the fat layer. Then, the pig ear was cut into a plurality of penetration membranes each having an area of $1.5 \times 1.5$ cm$^2$ and each having a thickness of 605 µm. The penetration membranes were soaked in phosphate buffer saline (PBS), were sealed in a bag, and were frozen for future use.

Figure 2:
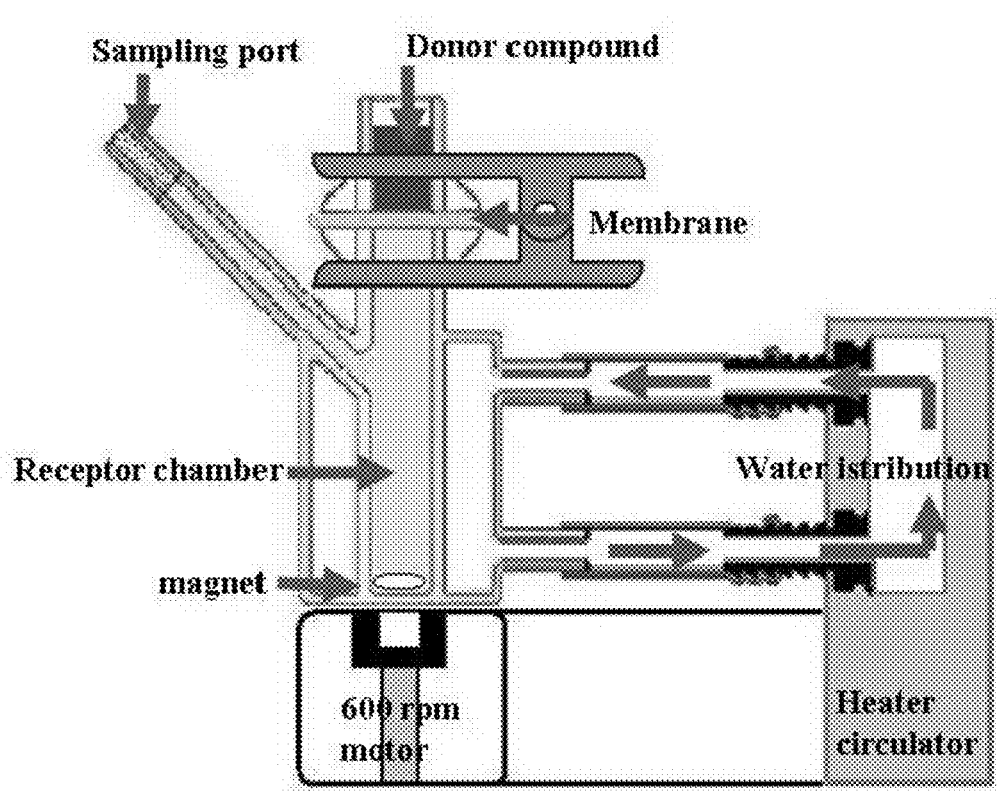
FIG. 2 is a schematic view of an in vitro transdermal testing system.
Figure 3:
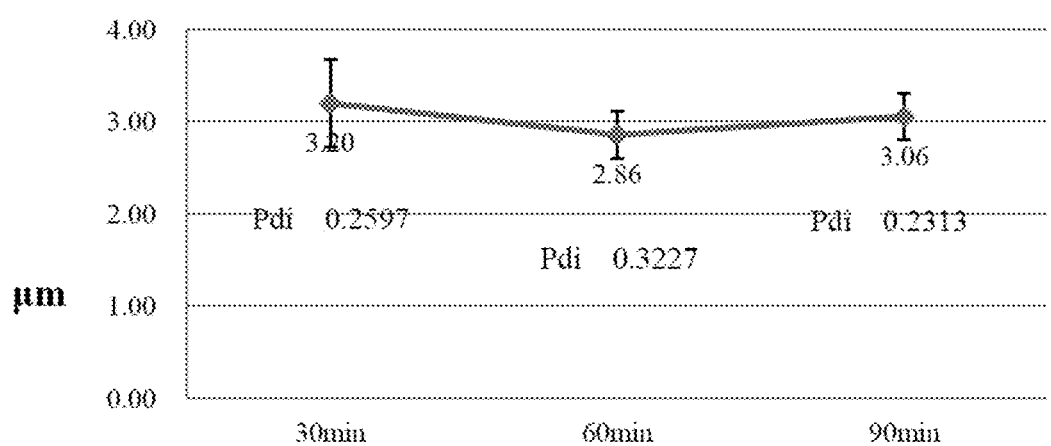
FIG. 3 is a diagram illustrating the affect to distribution of particle sizes of silica microcapsules by changing the stirring time of microemulsion polymerization.

(2) Before experiment, the penetration membranes were unfrozen in PBS to room temperature such that the gaps between the keratinocyte cells returned to their natural state. The penetration membranes were fixed in a Franz-type diffusion cell (see FIG. 2). The diffusion area was 0.636 cm$^2$. To test the skin integrity, the upper and lower sections of the diffusion cell were filled with 50% ethanol+50% PBS. After removing bubbles from the lower chamber, a sample of 0.5 g was placed into the upper, donor cell, and 50% ethanol+50% PBS was placed into the lower, receptor cell having a volume of 5.3 mL. A thermostat water tank heater was used to control the water temperature to be 35° C.±1. Stirring was carried out by using a magnet to balance the drug concentration distribution in the receptor cell.

(3) Each experiment used 5 diffusion cells to obtain the average value. 50 μL was sampled from the receptor cell and analyzed by HPLC. The same amount of a physiological solution was filled back into the receptor cell to maintain the total volume in the receptor cell.

(4) The injected volume was 50 μL. The detection wavelength was 260 nm. A mixture of 88% methanol, 11% water, and 1% acetic acid was used as the mobile phase in isocratic elution. The flow rate of the mobile phase was 1.0 mL/min. OMC of 1 ppm, 10 ppm, 50 ppm, and 100 ppm and avobenzone standard solution were used to create a calibration curve. Each concentration was detected three times to obtain the average value. Peak-ABC Chromatography Data Handling System (manufactured by Great Tide Instruments, Taiwan) was used to capture and handle the signals. A sample of 50 μL was sampled from the receptor cell and analyzed by HPLC. Peak-ABC Chromatography Data Handling System was used to analyze the concentration for calculating the lag time and the flux.

6. Sun Protection Test: The microcapsules according to the present invention were added into the sun protection formulation, and a sun protection factor instrument was used to measure the in vitro sun protection factor (SPF), exploring the defense ability to the ultraviolet rays. In the in vitro test, a 3M™ Transpore™ tape was used as artificial skin, coated with a UV filter at 2 mg/cm$^2$ application density, and irradiated by a solar simulation lamp of a SPF instrument to calculate assessment parameters including SPF, critical wavelength, curve area, UVA/UVB ratio, and Boots star rating.

7. Accelerated Photo-Stability Test: An ultraviolet radiator was used in the accelerated photo-stability test. The standard ultraviolet radiation is 17.5 J/cm$^2$ per hour. In examples, the samples were irradiated with 105 J/cm$^2$ per hour (6 times as large as 17.5 J/cm$^2$ per hour) and 315 J/cm$^2$ per hour (18 times as large as 17.5 J/cm$^2$ per hour) to rapidly access the stability of samples to screen ultraviolet rays.

In the first embodiment, the pH value was adjusted to be in a range between 2 and 1 (specifically 2, 1.5, and 1 in three examples). The smaller the pH value, the smaller the particle size. The minimal diameter of the particles was 1629.33±149.26 when the pH value was 1. The yield rates were respectively 79.6%, 80.8%, and 80.4% under different acid catalysis conditions at pH 2, pH 1.5, and pH 1. Since the yield rate (70.4%) at pH 1 was relatively low, pH 1.5 was selected as the optimal condition.

The yield rates were 79.6%, 80.0%, and 80.4% under different stirring times of 45 minutes, 60 minutes, and 90 minutes in the condensation procedure. The longer the stirring time, the smaller the particle size. The minimal diameter of the particles was 1689.33±252.16 when the stirring time was 90 minutes. Since there was no significant difference in the yield rates, 90 minutes was selected as the optimal stirring time.

The stirring speed and the stirring time in the sol-gel production procedure also affect the speed of hydrolysis and condensation. The more complete the hydrolysis was, the smaller the particle size was in the condensation procedure. When the TEOS molecules in the sol distributed more uniformly in condensation, the particle size was smaller and even during formation of the microcapsule.

The yield rates were 79.6% and 80.4% under different stirring speeds at 1000 rpm and 1400 rpm in the condensation. According to the results of particle size analysis, the faster the stirring speed in the condensation procedure, the smaller the particle size. The minimal diameter of the particles was 2540.00±37.36 when the stirring speed was 1400 rpm. Since there was no significant difference in the stirring speeds, 1400 rpm was selected as the optimal stirring speed. According to the results, the particle sizes were reduced significantly by increasing the stirring speed in the condensation procedure.

By comparing the affect of the stirring time in microemulsion polymerization, the optimal ratio between the water phase, oil phase and surfactants was 10:38.7:10.

The yield rates were 79.6%, 81.6%, and 83.2% under different stirring times of 30 minutes, 60 minutes, and 90 minutes in the microemulsion polymerization procedure. The longer the stirring time in the microemulsion polymerization, the higher the yield rate. The best yield rate was 83.2% when the stirring time was 90 minutes. Since there was no significant difference in the particle sizes, 90 minutes was selected as the optimal stirring time.

During emulsion, the stirring speed and the stirring time are considerable factors to the particle sizes and the completeness of emulsion. It is inferred that these parameters would affect the experimental results. The yield rate of the microcapsule according to the present invention would be increased if the stirring time is increased.

Figure 4:
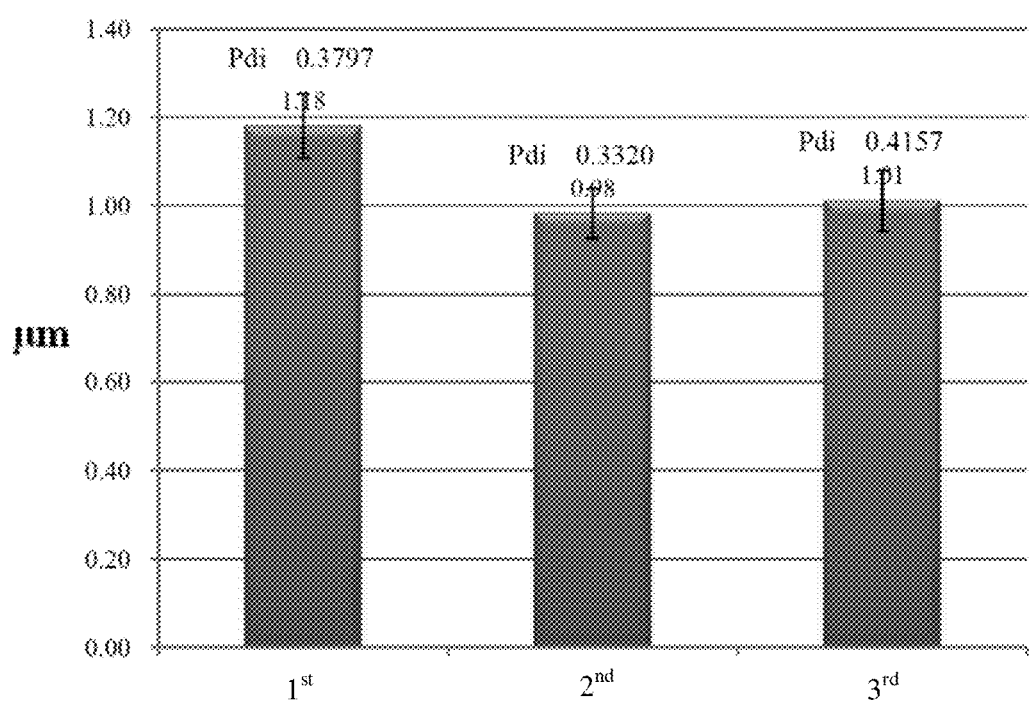
FIG. 4 is a diagram illustrating distribution of particle sizes of silica through three repeated preparations under the optimal conditions.

The yield rates were 79.6%, 80.4%, and 81.2% under different stirring speeds at 600 rpm, 1000 rpm, and 1400 rpm in the microemulsion polymerization procedure. According to the particle size analysis result (see FIG. 4), the faster the stirring speed in the microemulsion polymerization procedure, the smaller the particle size. The minimal diameter of the particles was 1636.67±182.44 when the stirring speed was 1400 rpm. Since there was no significant difference in the stirring speeds, 1400 rpm was selected as the optimal stirring speed.

In ordinary emulsion processes, the faster the emulsifying speed, the smaller the emulsified micelle.

In view of the foregoing, the optimal conditions for producing hollow silica microcapsule were as follows: acid catalysis at pH 1.5, the stirring speed and stirring time in the condensation procedure were respectively 1400 rpm and 90 minutes, and the stirring speed and stirring time in the microemulsion polymerization procedure were respectively 1400 rpm and 90 minutes. The procedures were repeated three times. The average yield rate was 82.73±0.31%. The average particle size of the three batches was 1058.00±106.93 nm According to the average particle size distributions and the yield rates of the products of the three batches, the optimal producing conditions possessed excellent reproducibility.

In the sun protection test on the first embodiment according to the present invention, the control sample was TiO$_2$ A100 (anatase TiO$_2$ without envelope treatment and produced by sulfuric acid method, with the anatase TiO$_2$ including more than 98.5% of TiO$_2$ and having a diameter of 0.16 μm).

The sun protection factor (SPF) is the time the UV sunscreen keeps the skin from reddening and sunburn on skin, which is an index of UVB protection.

SPF=MED with sunscreen/MED without sunscreen wherein MED is the minimal erythemal dose, namely, the minimal energy required for causing reddening of the skin exposed under UVB of a certain wavelength.

Hollow silica microcapsule powders were separately produced in three times. Then, three batches of SMC sunscreen samples were made from the silica microcapsule powders. The test results showed that the average SPF of SMC sunscreen was 11.27±0.08, and the average SPF of $TiO_2$ sunscreen (the comparative example) was 11.57±0.22.

The critical wavelength was the critical length of the UV filter. The curve area was the wavelength area covered by the UV filter. The critical wavelength is the wavelength at which the area under the absorbance curve represents 90% of the total area under the curve in the UV region. A critical wavelength of 370 nm or longer can be referred to as a broad spectrum. The critical wavelengths of SMC sunscreen and $TiO_2$ sunscreen were 362.95 nm and 358.73 nm, respectively. The curve areas of SMC sunscreen and $TiO_2$ sunscreen were 75.45 and 72.33, respectively. Namely, the results of SMC sunscreen and $TiO_2$ sunscreen were similar to each other.

The UVA/UVB ratio is the ratio of UVA protection effect to UVB protection effect. The higher the UVA/UVB ratio, the more effective the sun protection constituent against UVA.

The UVA/UVB ratio of SMC sunscreen was higher than that of $TiO_2$ sunscreen by 48%, as shown in Table 2. The sun protective ability of the hollow SMC carrier sunscreen without unentrapped chemical UV filter was approximately the same as that of a UV filter added with titanium dioxide. It is inferred that SMC sunscreen could be used to replace titanium oxide and has the potential of entrapping a chemical sun protection constituent to increase the sun protection effect while reducing the irritation and side effects of the chemical UV filter. Thus, the SMC sunscreen can be the main stream of future sun protection products.

TABLE 2

UV Protection Parameters of SMC Sunscreen and $TiO_2$ Sunscreen

|  | SMC sunscreen | $TiO_2$ sunscreen |
| --- | --- | --- |
| SPF | 11.27 ± 0.08 | 11.57 ± 0.22 |
| Critical Wavelength | 362.95 ± 2.00 | 385.73 ± 1.36 |
| Curve Area | 75.45 ± 3.67 | 72.33 ± 8.62 |
| UVA/UVB Ratio | 0.347 ± 0.011 | 0.234 ± 0.01 |
| Boots Star | 1 | 1 |

In the second embodiment of the present invention, more types of sunscreen were prepared and compared with O-SMC sunscreen and A-SMC sunscreen in this embodiment. The test results of the single chemical UV filter/silica microcapsule and the chemical UV filter complex/silica microcapsule were shown in Tables 3 and 4.

TABLE 3

O-SMC Sunscreen Formulation

| Ingredients (INCI) of formulation | | O-SMC sunscreen | SMC + OMC sunscreen | $TiO_2$ + OMC sunscreen | OMC sunscreen |
| --- | --- | --- | --- | --- | --- |
| Oil phase | Mineral oil | 10 | 10 | 10 | 10 |
| | Cyclomethicone (DC345) | 10 | 10 | 10 | 10 |
| | Sorbitan monooleate (Span 80) | 1 | 1 | 1 | 1 |
| | Cetyl PEG/PPG-10/1 Dimethicone (ABIL EM90) | 2 | 2 | 2 | 2 |
| | Germaben II* | 0.2 | 0.2 | 0.2 | 0.2 |
| | O-SMC (OMC silica microcapsule) | 10 | — | — | — |
| | SMC (silica microcapsule) | — | 7 | — | — |
| | Octyl methoxy-cinnamate (OMC) | — | 3 | 3 | 5 |
| Water phase | $TiO_2$ | — | — | 7 | — |
| | Glycerin | 10 | 10 | 10 | 10 |
| | water | 56.8 | 56.8 | 56.8 | 61.8 |

*Germaben II: Propylene Glycol/Diazolidinyl Urea/Methylparaben/Propylparaben

TABLE 4

A-SMC Sunscreen Formulation

| Ingredients (INCI) of formulation | | A-SMC sunscreen | SMC + avobenzone sunscreen | $TiO_2$ + avobenzone sunscreen | avobenzone sunscreen |
| --- | --- | --- | --- | --- | --- |
| Oil phase | Mineral oil | 10 | 10 | 10 | 10 |
| | Cyclomethicone (DC345) | 10 | 10 | 10 | 10 |
| | Sorbitan monooleate (Span 80) | 1 | 1 | 1 | 1 |
| | Cetyl PEG/PPG-10/1 Dimethicone (ABIL EM90) | 2 | 2 | 2 | 2 |
| | Germaben II* | 0.2 | 0.2 | 0.2 | 0.2 |
| | A-SMC (avobenzone silica microcapsule) | 10 | — | — | — |

TABLE 4-continued

A-SMC Sunscreen Formulation

| | Ingredients (INCI) of formulation | A-SMC sunscreen | SMC + avobenzone sunscreen | TiO$_2$ + avobenzone sunscreen | avobenzone sunscreen |
|---|---|---|---|---|---|
| | SMC (silica microcapsule) | — | 7 | — | — |
| | avobenzone | — | 3 | 3 | 5 |
| Water | TiO$_2$ | — | — | 7 | — |
| phase | Glycerin | 10 | 10 | 10 | 10 |
| | water | 56.8 | 56.8 | 56.8 | 61.8 |

*Germaben II: Propylene Glycol/Diazolidinyl Urea/Methylparaben/Propylparaben

A. OMC Silica Microcapsule (O-SMC)

1. Effect of OMC/TEOS Ratio on Preparation of O-SMC:

According to the research experience on SMC prepared by the sol-gel/emulsion technique under the optimal conditions according to the present invention, 5 g, 10 g, and 15 g of OMC (the OMC/TEOS ratios were 0.5:1, 1:1, and 1.5:1, respectively) were added to obtain O-SMC after condensation.

Figure 5:
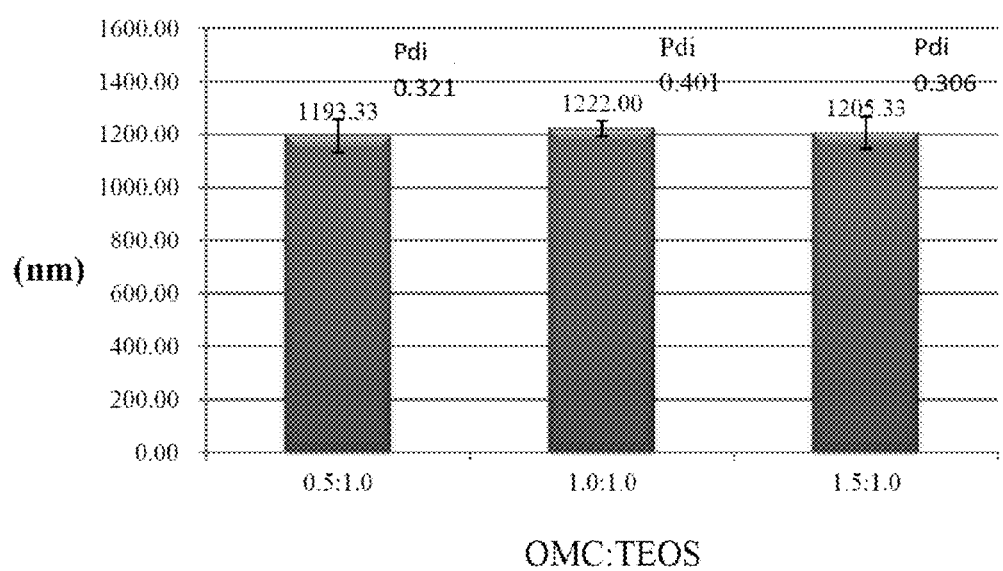
FIG. 5 is a diagram illustrating distribution of particle sizes of O-SMC carriers produced by using octyl methoxycinnamate (OMC) and tetraethoxysilane (TEOS) at different ratios.

FIG. 5 shows the test results. Different OMC/TEOS ratios did not cause significant difference in the particle sizes (1193.33±63.41 nm, 1222.00±28.58 nm, 1205.33±59.50 nm, respectively). It is inferred that addition of OMC does not affect the stability of the sol-gel process and, thus, does not affect the particle size.

Figure 6:
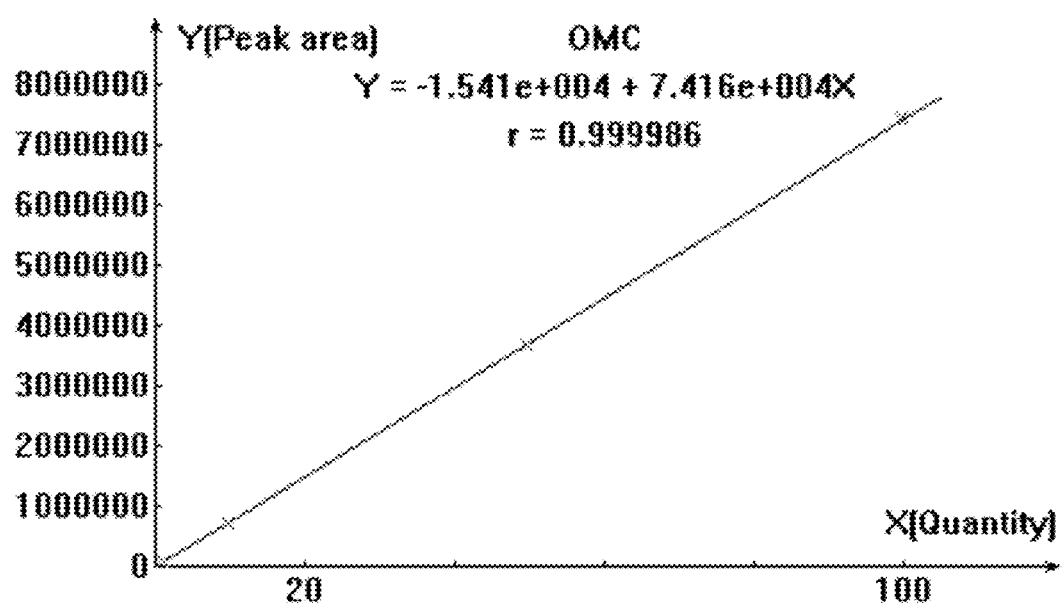
FIG. 6 is a calibration curve of OMC.

2. Effect of OMC/TEOS Ratio on Yield Rate, Entrapment Efficiency, and Capacity:

1-100 ppm OMC standard solutions were used to create a calibration curve, as shown in FIG. 6. Peak-ABC software was used to calculate the residual OMC concentration. Table 5 shows the affect of OMC/TEOS ratios on the yield rate, entrapment efficiency, and capacity. When the OMC/TEOS ratio was 0.5, the entrapment efficiency was the highest, but the capacity was the lowest, which meant that the amount of OMC contained in each gram of powders was the least. When the OMC/TEOS ratio was 1.5, the capacity was the highest, but the entrapment efficiency was the lowest, which meant that the production wasted the most OMC. Considering the entrapment efficiency, capacity, and the production costs, the optimal OMC/TEOS ratio was selected to be 1.

TABLE 5

Yield Rate, Entrapment Rate, and Capacity of O-SMC Carriers Prepared under Different OMC/TEOS Ratios

| | OMC/TEOS = 0.5 | OMC/TEOS = 1.0 | OMC/TEOS = 1.5 |
|---|---|---|---|
| Yield rate | 66.70 ± 0.16% | 57.98 ± 1.14% | 48.15 ± 0.51% |
| Entrapment rate | 33.69 ± 0.47% | 32.77 ± 2.28% | 24.78 ± 0.86% |
| Capacity | 16.84 ± 0.20% | 28.24 ± 1.41% | 30.88 ± 0.73% |

3. Reproducibility of Preparation of O-SMC:

The products were repeatedly produced three times under the optimal conditions. The average particle size of the three batches was 1183.22133.53 nm, and the relative standard deviation (RSD) was 2.83%. The average yield rate of the three batches was 57.9210.27% (RSD was 0.79%). The entrapment efficiency was 32.6410.55% (RSD was 1.68%). The capacity was 28.17±0.34 (RSD was 1.21%). According to the yield rates of the products of the three batches, the preparation conditions possessed excellent reproducibility.

4. In Vitro Transdermal Delivery of O-SMC:

The Franz-type diffusion cell system was used to assess the penetration characteristics of carrier-entrapped filters. The transdermal absorption curve was observed for 4 hours. The stratum corneum is an important barrier of the skin for resisting alien objects and is also a hindrance to transdermal delivery of an active constituent. During an initial stage of passage from the donor site to the receptor site through the skin, there is a lag time for the active constituent to penetrate the membrane of the saturated skin. After that, the active constituent remains in steady-state diffusion for a period of time during which the diffusion flux is not changed.

Assume the concentrations of the active constituent at the donor site and the receptor site of the penetration membrane are respectively Cv and Cr, the mechanism of initial transdermal absorption can be explained by Fick's first law of diffusion:

$$J = dQ/Dt = DAK(Cv-Cr)/h$$

wherein J is the transdermal flux, Q is the cumulative penetration amount, D is the diffusion coefficient, A is the diffusional surface area, K is the partition coefficient, and h is the diffusional pathlength.

Since Cr is very small at the initial stage of penetration, DC=(Cv−Cr) arrpoximates Cv. The transdermal flux is in proportion to the concentration difference (J=K). Thus, the slope of an optimal line in a diagram obtained from the cumulative penetration quantity Q and the penetration time t is the transdermal flux J. The lag time parameter can be obtained by linear extrapolation to the intersection on X axis.

0.5 g of sun protection mixture containing OMC (mineral oil: OMC=97:3) and 0.5 g of sun protection mixture containing O-SMC (mineral oil : O-SMC=90:10) were used. 50% PBS +50% alcohol was used as the lotion in the receptor site. After calculation of the results, OMC did not penetrate. The transdermal flux of unentrapped OMC having the same concentration was 40.069 μg/cm2·hr. The lag time was 0.15 hr. According to the penetration curve and the transdermal flux shown in Table 6, entrapped O-SMC can provide long-term protection without causing allergy through transdermal absorption.

TABLE 6

In Vitro Trandermal Delivery Data of O-SMC in 6 hours

| | OMC | | O-SMC | |
|---|---|---|---|---|
| Time Hour | Transdermal flux (%) | Amount in receptor site ($\mu g/cm^2$) | Transdermal flux (%) | Amount in receptor site ($\mu g/cm^2$) |
| 0 | 0 | 0 | 0 | 0 |
| 0.5 | 0 | 0 | 0 | 0 |
| 1 | 0.13 ± 0.01 | 31.84 ± 1.81 | 0 | 0 |
| 2 | 0.28 ± 0.03 | 65.15 ± 7.96 | 0 | 0 |
| 3 | 0.52 ± 0.02 | 121.97 ± 4.95 | 0 | 0 |
| 6 | 0.96 ± 0.05 | 227.55 ± 12.94 | 0 | 0 |

5. In Vitro UV Protection of Sunscreen:

(1) UVB Protection Ability Assessment: The products were repeatedly produced three times under the optimal conditions. The sun protection effects of the three batches were very close to the average SPF (20.21±0.06) of the three batches, and the relative standard deviation (RSD) was 0.30%. This means that the production procedure possesses excellent reproducibility and is in positive correlation to the entrapment efficiency and the capacity.

Table 7 shows the results of O-SMC sunscreen and the control samples (SMC sunscreen, $TiO_2$ sunscreen, and OMC sunscreen). The SPF of O-SMC was 20.21±0.06, which was larger than the SPF (17.26±0.80) of SMC+OMC sunscreen by 17.09%, was larger than the SPF (17.61±0.62) of $TiO_2$+OMC sunscreen by 14.76%, and was larger than the SPF (15.63±0.68) of OMC sunscreen by 29.30%.

(2) UVA Protection Ability Assessment:

The critical wavelength was the critical length of the UV filter. The curve area was the wavelength area covered by the UV filter. The critical wavelength is the wavelength at which the area under the absorbance curve represents 90% of the total area under the curve in the UV region. A critical wavelength of 370 nm or longer can be referred to as a broad spectrum. As can be seen from Table 7, the critical wavelengths of O-SMC sunscreen, SMC+OMC sunscreen, TiO2+OMC sunscreen, and OMC sunscreen were 344.92±3.30 nm, 350.93±2.97 nm, 349.83±3.72, and 333.33±1.33 nm, respectively. The four sets had similar results. The curve areas of O-SMC sunscreen, SMC+OMC sunscreen, TiO2+OMC sunscreen, and OMC sunscreen were 109.15±2.01, 92.58±0.38, 92.39±1.01, and 100.93±1.14, respectively. The experiment samples (O-SMC sunscreen) were obviously superior to the three control samples.

The UVA/UVB ratio is the ratio of UVA protection effect to UVB protection effect. The higher the UVA/UVB ratio, the more effective the sun protection ability against UVA, as mentioned above. Boots is the Boots star rating of UVA/UVB. The UVA/UVB ratio of O-SMC sunscreen was 0.23, which was close to the UVA/UVB ratio (0.22) of SMC+OMC sunscreen and the UVA/UVB ratio (0.21) of $TiO_2$+OMC sunscreen and was superior to the UVA/UVB ratio (0.22) of OMC sunscreen (Table 7). Namely, both of $TiO_2$ shell and $TiO_2$ can provide UVA protection. As a result, the UVA/UVB ratio of the control sample including only OMC was the worst.

The research showed that the UVB protection ability and the UVA protection ability of the O-SMC sunscreen added with entrapped chemical UV filters were obviously superior to those of the control samples (SMC+OMC sunscreen, $TiO_2$+OMC sunscreen, and OMC sunscreen).

TABLE 7

UV Protection Parameters of O-SMC Sunscreen, SMC + OMC Sunscreen, $TiO_2$ + OMC Sunscreen, & OMC Sunscreen

| | O-SMC sunscreen | SMC + OMC sunscreen | $TiO_2$ + OMC sunscreen | OMC sunscreen |
|---|---|---|---|---|
| SPF | 20.21 ± 0.06 | 17.26 ± 0.80 | 17.61 ± 0.62 | 15.63 ± 0.68 |
| Critical Wavelength | 344.92 ± 3.30 | 350.93 ± 2.97 | 349.83 ± 3.72 | 333.33 ± 1.33 |
| Curve Area | 109.15 ± 2.01 | 92.58 ± 0.38 | 92.39 ± 1.01 | 100.93 ± 1.14 |
| UVA/UVB Ratio | 0.23 ± 0.00 | 0.22 ± 0.01 | 0.21 ± 0.02 | 0.16 ± 0.02 |
| Boots Star | 1 | 1 | 1 | 0 |

6. Stability Test of Sunscreen:

Chemical UV filters are apt to become less inactive or even destructed under irradiation with UV rays. Thus, we expected the chemical UV filters entrapped by silica to be more stable and even provide long-term protection. Since OMC is a UVB filter, degradation of SPF of OMC was used as the standard. As can be seen from Table 8, after irradiation with 315 $J/cm^2$, the UV protection ability of O-SMC sunscreen degraded by 16.54%, which was obviously smaller than the degradation percentages of SMC+OMC sunscreen (29.20%), $TiO_2$+OMC sunscreen (28.46%), and OMC sunscreen (35.25%). It is inferred that the OMC UV filter rapidly lost protection soon after irradiation by UV rays.

Since physical UV filters were added into the SMC+OMC sunscreen and TiO2+OMC sunscreen of the control samples, a certain protection was left after irradiation by UV rays. Although having the same content of OMC and silica as SMC sunscreen, O-SMC sunscreen was obviously superior to SMC sunscreen in UV protection (the SPF of O-SMC sunscreen was 20.21, the SPF of SMC+OMC sunscreen was 17.26) and stability (the degradation percentage of O-SMC sunscreen was 16.54%, the degradation percentage of SMC+OMC sunscreen was 29.20%). Thus, it is inferred that the combined physical-chemical UV filter provides the chemical UV filter with a synergistic effect to obtain enhanced protection while providing the chemical UV filter with enhanced stability to provide longer protection.

Under destruction by irradiation with a LTV lamp, the degradation extents of the other three sunscreens were obviously higher than that of O-SMC sunscreen. Thus, it is proven that OMC entrapped by silica obviously protects the chemical UV filter, reducing instability and photo-decomposition of chemical UV filter per se.

TABLE 8

Destruction of O-SMC Sunscreen by UV Radiation Intensity of 315 J/cm$^2$

| | O-SMC sunscreen | SMC + OMC sunscreen | TiO$_2$ + OMC sunscreen | OMC sunscreen |
|---|---|---|---|---|
| Original SPF | 20.21 ± 0.06 | 17.26 ± 0.80 | 17.61 ± 0.62 | 15.63 ± 0.68 |
| SPF after 315 J/cm$^2$ | 16.87 ± 0.41 | 12.22 ± 0.34 | 12.60 ± 0.37 | 10.12 ± 0.21 |
| Destructing Degradation percentage | 26.72% | 34.71% | 33.36% | 46.18% |

B. Avobenzone Silica Microcapsule (A-SMC)

1. Affect of Avobenzone/TEOS Ratio on Preparation of A-SMC:

According to the research experience on SMC prepared by the sol-gel/emulsion technique under the optimal conditions according to the present invention, 5 g, 10 g, and 15 g of avobenzone (the avobenzone/TEOS ratios were 0.5:1, 1:1, and 1.5:1, respectively) were added to obtain A-SMC after condensation.

Figure 7:
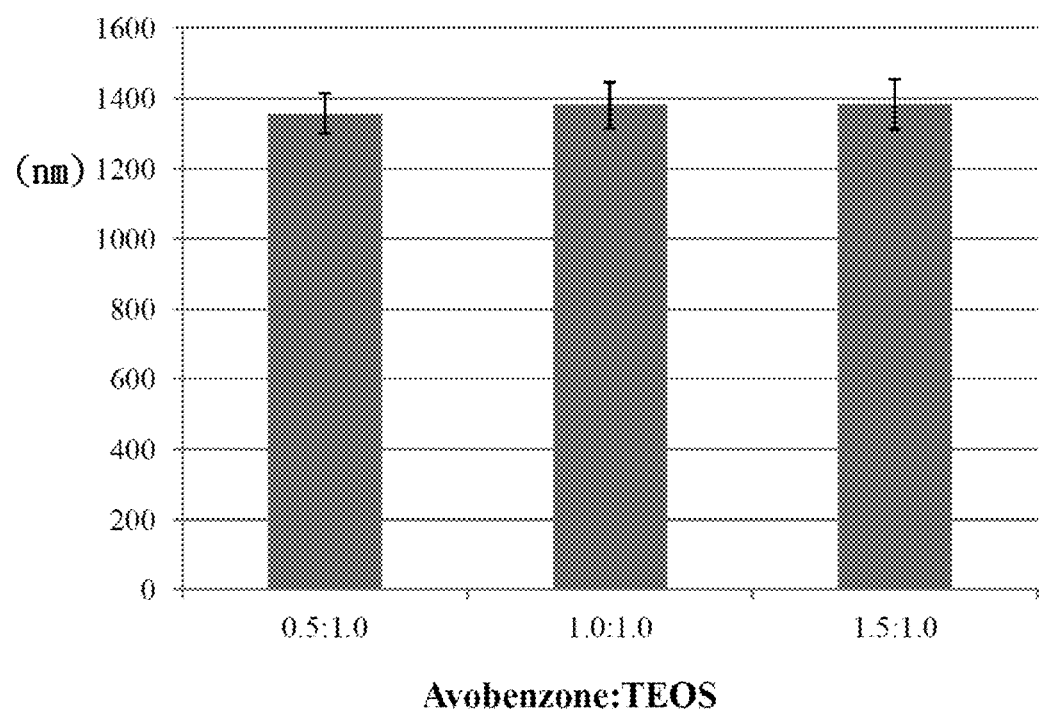
FIG. 7 is a diagram illustrating particle sizes of A-SMC produced by using avobenzone and tetraethoxysilane at different ratios.

FIG. 7 shows the test results. Different avobenzone/TEOS ratios did not cause significant difference in the particle sizes (1357.67±56.87 nm, 1381.00±65.48 nm, 1383.33±71.43 nm, respectively). It is inferred that addition of avobenzone does not affect the stability of the sol-gel process and, thus, does not affect the particle size. However, the particle size of A-SMC was larger than that of O-SMC, and this could be the reason why OMC has higher solubility in alcohol than A-SMC.

Figure 8:
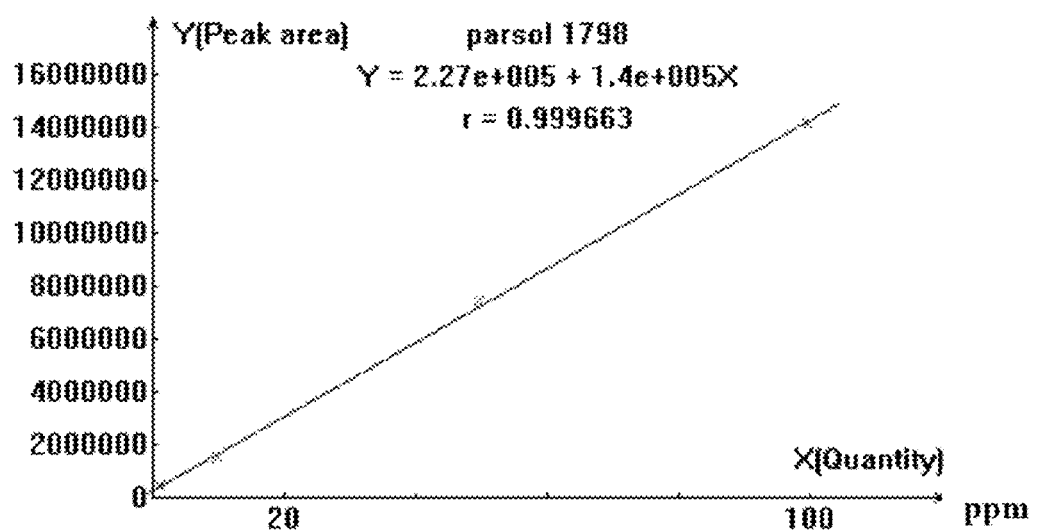
FIG. 8 is a calibration curve of avobenzone.

2. Affect of Avobenzone/TEOS Ratio on Yield Rate, Entrapment Efficiency, and Capacity:

1-100 ppm standard solutions of avobenzone were used to create a calibration curve, as shown in FIG. 8. Table 9 shows the affect of avobenzone/TEOS ratio on the yield rate, entrapment efficiency, and capacity. When the avobenzone/TEOS ratio was 0.5, the entrapment efficiency was the highest, but the capacity was the lowest, which meant that the amount of avobenzone contained in each gram of powders was the least. When the avobenzone/TEOS ratio was 1.5, the capacity was the highest, but the entrapment efficiency was the lowest, which meant that the production process could waste avobenzone. Considering the entrapment efficiency, capacity, and the production costs, the optimal avobenzone/TEOS ratio was selected to be 1.

3. Reproducibility of Preparation of A-SMC:

The products were repeatedly produced in three times under the optimal conditions. The average particle size of the three batches was 1351.33±37.31 nm, and the relative standard deviation (RSD) was 2.76%. The average yield rate of the three batches was 55.50±0.38% (RSD was 0.68%). The entrapment efficiency was 30.99±0.75% (RSD was 2.43%). The capacity was 27.80±0.38 (RSD was 1.37%). According to the yield rates of the products of the three batches, the preparation conditions possessed excellent reproducibility.

4. In Vitro Transdermal Delivery of A-SMC:

The Franz-type diffusion cell system was used to assess the penetration characteristics of carrier-entrapped filters. The transdermal absorption curve was observed for 6 hours. 0.5 g of sun protection mixture containing avobenzone (mineral oil: avobenzone=97:3) and 0.5 g of sun protection mixture containing A-SMC (mineral oil: A-SMC=90:10) were used. 50% PBS+50% alcohol was used as the lower layer. After calculation, the results are shown in Table 9 and indicate that A-SMC did not have avobenzone penetration. The transdermal flux of unentrapped avobenzone having the same concentration was 28.237 µg/cm$^2$·hr. The lag time was 0.23 hr. According to the penetration curve and the transdermal flux shown in Table 9, entrapped avobenzone can provide long-term protection without causing allergic reaction through transdermal absorption.

TABLE 9

In Vitro Transdermal Delivery Data of A-SMC in 6 hours

| | avobenzone | | A-SMC | |
|---|---|---|---|---|
| Time Hour | Transdermal flux (%) | Amount in receptor site (µg/cm$^2$) | Transdermal flux (%) | Amount in receptor site (µg/cm$^2$) |
| 0 | 0 | 0 | 0 | 0 |
| 0.5 | 0 | 0 | 0 | 0 |
| 1 | 0.09 ± 0.01 | 20.12 ± 2.19 | 0 | 0 |
| 2 | 0.20 ± 0.01 | 48.21 ± 2.73 | 0 | 0 |
| 3 | 0.36 ± 0.02 | 84.85 ± 4.27 | 0 | 0 |
| 6 | 0.68 ± 0.02 | 161.26 ± 3.74 | 0 | 0 |

5. In Vitro UV Protection of Sunscreen:

(1) UVB Protection Ability Assessment: The control sample in this research was TiO$_2$ A100 (anatase TiO$_2$ without envelope treatment and produced by sulfuric acid method, with the anatase TiO$_2$ including more than 98.5% of TiO$_2$ and having a diameter of 0.16 µm).

The products were repeatedly produced three times under the optimal conditions. The sun protection effects of the three batches were very close to the average SPF (14.97±0.32) of the three batches, and the relative standard deviation (RSD) was 2.12%. This means that the production procedure possesses excellent reproducibility and is in positive correlation to the entrapment efficiency and the capacity.

Table 10 shows the results of A-SMC sunscreen and the comparative examples (SMC+avobenzone sunscreen, TiO$_2$+avobenzone sunscreen, and avobenzone sunscreen). The SPFs of A-SMC, TiO$_2$+avobenzone sunscreen, and SMC+OMC sunscreen were respectively 14.97±0.32, 13.18±0.19, and 12.7±0.43, all of which were obviously superior to the SPF (3.74±0.15) of avobenzone.

(2) UVA Protection Ability Assessment:

As can be seen from Table 10, the critical wavelengths of A-SMC sunscreen, SMC+avobenzone sunscreen, TiO$_2$+avobenzone sunscreen, and avobenzone sunscreen were 376.22±2.32 nm, 374.93±2.17 nm, 376.19±3.11, and 379.62±1.38 nm, respectively. The curve areas of A-SMC sunscreen, SMC+avobenzone sunscreen, TiO$_2$+avobenzone sunscreen, and avobenzone sunscreen were 101.72±1.93, 98.52±0.71, 99.23±1.62, and 98.25±1.01, respectively. The four sets had similar results.

The UVA/UVB ratio of A-SMC sunscreen was 0.80±0.02, which was superior to the UVA/UVB ratio (0.62±0.01) of SMC+avobenzone sunscreen and the UVA/UVB ratio (0.60±0.01) of TiO$_2$+avobenzone sunscreen. It was found that the UVA absorption value of A-SMC sunscreen was obviously superior to the other three sets. When avobenzone and a physical UV filter were both added in a product, precipitation and degradation have occurred sometimes. Thus, although 3 g of SMC+avobenzone sunscreen and 3 g of TiO$_2$+avobenzone sunscreen (the control samples) contained more avobenzone than 2.82 g of A-SMC, the UVA protection was not as good as entrapped ones and was even worse than avobenzone sunscreen.

The research showed that the UVB protection ability and the UVA protection ability of the A-SMC sunscreen added with entrapped chemical UV filter were obviously superior to those of the control samples (SMC+avobenzone sunscreen, $TiO_2$+avobenzone sunscreen, and avobenzone sunscreen).

TABLE 10

UV Protection of A-SMC Sunscreen & Control Samples

|  | A-SMC sunscreen | SMC + avobenzone sunscreen | $TiO_2$ + avobenzone sunscreen | avobenzone sunscreen |
|---|---|---|---|---|
| Original SPF | 14.97 ± 0.32 | 13.18 ± 0.19 | 12.7 ± 0.43 | 3.74 ± 0.15 |
| Critical Wavelength | 376.22 ± 2.32 | 374.93 ± 2.17 | 376.19 ± 3.11 | 379.62 ± 1.38 |
| Curve Area | 101.72 ± 1.93 | 98.52 ± 0.71 | 99.23 ± 1.62 | 98.25 ± 1.01 |
| UVA/UVB Ratio | 0.80 ± 0.02 | 0.62 ± 0.01 | 0.60 ± 0.01 | 1.58 ± 0.04 |
| Boots Star | 3 | 2 | 2 | 4 |

6. Stability Test of Sunscreen:

Since avobenzone is a UVA filter, the UVB protection mainly comes from the physical UV filter. Observation was focused on destruction of UVA protection after irradiation. Since the wavelength of 360 nm has the maximal absorption value, the absorption marker is represented by 360 nm. As can be seen from Table 11, after irradiation with 315 $J/cm^2$, the UV protection ability of A-SMC sunscreen degraded by 32.94%, which was obviously superior to the degradation percentages of SMC+avobenzone sunscreen (55.24%), $TiO_2$+avobenzone sunscreen (65.68%), and avobenzone sunscreen (85.76%).

Since physical UV filters were added into SMC+avobenzone sunscreen ($ABS_{360}$ was reduced by 43.74%) and $TiO_2$+avobenzone sunscreen ($ABS_{360}$ was reduced by 44.67%) of the control samples, a certain UVA protection was left after irradiation by UV rays. Due to the instability of avobenzone with respect to light and other ingredients in formulation, avobenzone sunscreen ($ABS_{360}$ was reduced by 66.67%) had the maximal reduction. Entrapped A-SMC ($ABS_{360}$ was reduced by 30.00%) had the minimal reduction. This proves that entrapped avobenzone can avoid the adverse affect resulting from conflict with the formulation, further protecting avobenzone from rapid destruction by irradiation.

TABLE 11

Destruction of A-SMC Sunscreen by UV Radiation Intensity of 315 $J/cm^2$

|  | A-SMC sunscreen | SMC + avobenzone sunscreen | $TiO_2$ + avobenzone sunscreen | avobenzone sunscreen |
|---|---|---|---|---|
| Original $Abs_{360}$ | 0.950 | 0.631 | 0.591 | 0.777 |
| $Abs_{360}$ after 315 $J/cm^2$ | 0.665 | 0.355 | 0.327 | 0.259 |
| Degradation percentage | 30.00% | 43.74% | 44.67% | 66.67% |

In the third embodiment of the present invention, a plurality of UV filters was mixed as a compound UV filter. The UV filters can be chemical UV filters. In this embodiment, the UV filters included OMC, avobenzone, and BP-3, all of which are chemical UV filters. The compound microcapsule produced was referred to as OAB-SMC for short. The following analyses were conducted.

1. Reproducibility of OAB-SMC:

According to the research experience on SMC prepared by the sol-gel/emulsion technique under the optimal conditions according to the present invention, OMC, avobenzone, and BP-3 were added in the ratio of 5:3:2 (OMC:avobenzone:BP-3: TEOS=0.5:0.3:0.2:1). The products were repeatedly produced three times under the optimal conditions. The average particle size of the three batches was 1202.22±40.14 nm, and the relative standard deviation (RSD) was 3.34%. The average yield rate of the three batches was 56.03±0.44% (RSD was 0.47%). According to the yield rates of the products of the three batches, the preparation conditions possessed excellent reproducibility.

2. In Vitro UV Protection of Sunscreen:

(1) UVB Protection Ability Assessment: The products were repeatedly produced three times under the optimal conditions. The sun protection effects of the three batches were very close to the average SPF (25.82±0.67) of the three batches, and the relative standard deviation (RSD) was 2.59%.

Table 12 shows the results of OAB-SMC sunscreen and the control samples (SMC+OAB sunscreen, $TiO_2$+avobenzone sunscreen, and avobenzone sunscreen). The SPF of OAB-SMC sunscreen was 25.82±0.67, which was superior to the SPF (22.56±0.46) of SMC+OAB and the SPF (21.40±0.54) of $TiO_2$+OAB sunscreen, and was very close to the SPF (23.17±0.30) of OAB sunscreen. It is proven that addition of silica microcapsules increases the UV protection ability and reduces the amount of chemical UV filters. Furthermore, entrapment can avoid degradation of some chemical UV filters resulting from instability with respect to the formulation.

(2) UVA Protection Ability Assessment:

As can be seen from Table 12, the critical wavelengths of OAB-SMC sunscreen, SMC+OAB sunscreen, $TiO_2$+OAB sunscreen, and OAB sunscreen were 373.52±2.37 nm, 375.53±1.97 nm, 370.29±2.15, and 370.92±1.88 nm, respectively. The curve areas of OAB-SMC sunscreen, SMC+OAB sunscreen, $TiO_2$+OAB sunscreen, and OAB sunscreen were 100.86±2.17, 99.82±0.71, 98.93±1.93, and 99.28±2.03, respectively. The four sets had similar results.

The UVA/UVB ratio of OAB-SMC sunscreen was 0.70±0.03, which was superior to the UVA/UVB ratio (0.5±0.02) of SMC+OAB sunscreen and the UVA/UVB ratio (0.44±0.01) of $TiO_2$+OAB sunscreen. It was found that the UVA absorption of OAB-SMC sunscreen was obviously superior to that of SMC+OAB sunscreen and $TiO_2$+OAB sunscreen.

TABLE 12

UV Protection of OAB-SMC Sunscreen & Control Samples

|  | OAB-SMC sunscreen | SMC + OAB sunscreen | TiO$_2$ + OAB sunscreen | OAB sunscreen |
|---|---|---|---|---|
| SPF | 25.82 ± 0.67 | 22.56 ± 0.46 | 21.40 ± 0.54 | 23.17 ± 0.30 |
| Critical Wavelength | 375.52 ± 2.37 | 375.53 ± 1.97 | 370.29 ± 2.15 | 370.92 ± 1.88 |
| Curve Area | 100.86 ± 2.17 | 99.82 ± 1.53 | 98.93 ± 1.93 | 99.28 ± 2.03 |
| UVA/UVB Ratio | 0.70 ± 0.03 | 0.5 ± 0.02 | 0.49 ± 0.01 | 0.78 ± 0.03 |
| Boots Star | 3 | 2 | 2 | 3 |

3. Stability Test of Sunscreen:

Chemical UV filters are apt to become less inactive or even destructed under irradiation with UV rays. Thus, we expected the chemical UV filters entrapped by silica to be more stable and even provide long-term protection. Degradation of UVB protection utilized SPF as the index while UVA protection was referenced by the absorption value at 360 nm with regard to A-SMC.

As can be seen from Table 13, the degradation (degradation percentage was 26.72%, ABS360 was reduced by 29.98%) of entrapped OAB-SMC sunscreen was obviously smaller than the other three sets. Particularly, although OAB sunscreen without physical UV filters (the comparative example) had good UV protection in the beginning, the degradation (degradation percentage was 46.18%, ABS360 was reduced by 67.91%) of OAB sunscreen became the largest after irradiation with UV rays due to instability of chemical UV filters. Considering the UV protection and stability, it was found that the protection ability of chemical UV filters were better than physical UV filters. Furthermore, OMC can help uniform solution and distribution of other UV filters in the formulation. Thus, the compound chemical UV filters can achieve higher and complete UV protection. Since the activity of chemical UV filters rapidly degrades soon after irradiation by UV rays and since the activity of chemical UV filters weakens after contact with air, the UV protection of chemical UV filters without physical UV filters will significantly degrade when irradiated with UV rays, failing to provide long-term protection.

TABLE 13

Destruction of OAB-SMC Sunscreen by UV Radiation Intensity of 315 J/cm$^2$

|  | OAB-SMC sunscreen | SMC + OAB sunscreen | TiO$_2$ + OAB sunscreen | OAB sunscreen |
|---|---|---|---|---|
| Original SPF | 25.82 ± 0.67 | 22.56 ± 0.46 | 21.40 ± 0.54 | 23.17 ± 0.30 |
| Original Abs$_{360}$ | 0.8940 | 0.7490 | 0.7490 | 1.0190 |
| 315 J/cm2 Destructing SPF | 18.92 ± 0.81 | 14.73 ± 0.52 | 14.26 ± 0.43 | 12.47 ± 0.37 |
| Degradation percentage | 26.72% | 34.71% | 33.36% | 46.18% |
| Abs$_{360}$ after 315 J/cm2 | 0.626 | 0.391 | 0.324 | 0.327 |
| Degradation percentage | 29.98% | 47.80% | 56.74% | 67.91% |

C. Compound OMC, Avobenzone, Tinosorb M, and DHHB silica microcapsule (OATD-SMC)

1. Formulation Selection:

OMC, Avobenzone, Tinosorb M, and DHHB were added into the formulation in different ratios. The ratio of the UV filters for producing the complex silica microcapsule was decided by the sun protection ability of the formulation.

After preparation, the protection ability of the UV filter formulation was tested with a SPF instrument, and the results are shown in Table 14. As can be seen from Table 14, UV filter formulation 2 has higher SPF and higher UVA/UVB. It is determined that the UV filter ratio of UV filter formulation 2 is better. Thus, OATD-SMC is produced in which the ratio between OMC, avobenzone, Tinosorb M, and DHHB was 5:3:1:1.

2. Reproducibility of OATD-SMC:

According to the above experiment, OMC, avobenzone, Tinosorb M, and DHHB were added in a ratio of 5:3:1:1 (OMC:avobenzone:Tinosorb M:DHHB:TEOS=0.5:0.3:0.1:0.1:1) at this stage. After three times of repeated productions, the average particle size of the three batches was 1222.11±21.99 nm, and the relative standard deviation (RSD) was 1.80%. The average yield rate of the three batches was 56.20±0.50% (RSD was 0.89%). According to the yield rates of the products of the three batches, the preparation conditions possessed excellent reproducibility.

TABLE 14

UV Protection of UV Filter Complex Formulation

|  | Chemical UV filter Formula 1 | Chemical UV filter Formula 2 |
|---|---|---|
| SPF | 36.57 ± 0.76 | 38.41 ± 1.31 |
| Critical Wavelength | 374.52 ± 1.49 | 381.15 ± 1.57 |
| Curve Area | 105.16 ± 1.01 | 110.52 ± 1.14 |
| UVA/UVB Ratio | 0.75 ± 0.02 | 0.96 ± 0.04 |
| Boots | 3 | 4 |

3. In Vitro UV Protection of Sunscreen: (1) UVB Protection Ability Assessment: The products were repeatedly produced three times under the optimal conditions. The sun protection effects of the three batches were very close to the average SPF (30.03±0.97) of the three batches, and the relative standard deviation (RSD) was 3.24%. Table 15 shows the results of OATB-SMC sunscreen and the control samples (SMC+OATD sunscreen, TiO$_2$+OATD sunscreen, and OATD sunscreen). The SPF of OATD-SMC sunscreen was 30.03±0.97, which was superior to the SPF (25.69±0.51) of SMC+OATD and the SPF (26.07±0.99) of TiO$_2$+OATD sunscreen, and was very close to the SPF (30.16±0.76) of OATD sunscreen containing a higher amount of chemical UV filter. It is proven that addition of silica microcapsule increases the UV protection ability and reduces the required amount of chemical UV filter. Furthermore, entrapment can avoid degradation of some chemical UV filters, which results from instability with respect to the formulation.

(2) UVA Protection Ability Assessment:

As can be seen from Table 15, the critical wavelengths of OATD-SMC sunscreen, SMC+OATD sunscreen, TiO$_2$+OATD sunscreen, and OATD sunscreen were 378.13±1.55 nm, 374.89±1.01 nm, 375.62±1.17, and 378.65±1.42 nm, respectively. The curve areas of OATD-SMC sunscreen, SMC+OATD sunscreen, TiO$_2$+OATD sunscreen, and OATD sunscreen were 100.86±2.17, 99.82±1.53, 98.93±1.93, and 99.28±2.03, respectively. The four sets had similar results.

TABLE 15

UV Protection of OATD-SMC Sunscreen and Comparative Examples

|  | OATD-SMC sunscreen | SMC + OATD sunscreen | TiO$_2$ + OATD sunscreen | OATD sunscreen |
|---|---|---|---|---|
| SPF | 30.04 ± 0.97 | 25.69 ± 0.51 | 26.07 ± 0.99 | 30.16 ± 0.76 |
| Critical Wavelength | 378.13 ± 1.55 | 374.89 ± 1.01 | 375.62 ± 1.17 | 378.65 ± 1.42 |
| Curve Area | 100.86 ± 2.17 | 99.82 ± 1.53 | 98.93 ± 1.93 | 99.28 ± 2.03 |
| UVA/UVB Ratio | 0.75 ± 0.03 | 0.65 ± 0.02 | 0.60 ± 0.02 | 0.81 ± 0.04 |
| Boots Star | 3 | 2 | 2 | 3 |

4. Stability Test of Sunscreen:

Chemical UV filters are apt to become less inactive or even destructed under irradiation with UV rays. Thus, we expected the chemical UV filters entrapped by silica to be more stable and even provide long-term protection. Since this formula was a complex formulation of UV filters against UVB and UVA, degradation of UVB protection utilized SPF as the index while UVA protection was referenced by the absorption value at 360 nm with regard to A-SMC.

As can be seen from Table 16, the degradation (degradation percentage was 20.64%, ABS360 was reduced by 28.41%) of entrapped OATD-SMC sunscreen was obviously smaller than SMC+OATD sunscreen (degradation percentage was 25.85%, ABS360 was reduced by 40.96%), TiO2+OATD sunscreen (degradation percentage was 27.92%, ABS360 was reduced by 40.99%), and OATD sunscreen (degradation percentage was 46.18%, ABS360 was reduced by 67.91%). Particularly, although OATD sunscreen without physical UV filters (the comparative example) had good UV protection in the beginning, the degradation of OATD sunscreen became the largest after irradiation with UV rays due to instability of chemical UV filters. Considering the UV protection and stability, the protection ability of chemical UV filters is better than physical UV filters. Furthermore, OMC can help uniform solution and distribution of other UV filters in the formulation. Thus, the chemical UV filters complex can achieve higher and complete UV protection. Since the activeness of chemical UV filters rapidly degrades soon after irradiation by UV rays and since the activity of chemical UV filters weakens after contact with air, the protection of chemical UV filters without physical UV filters will significantly degrade when irradiated with UV rays, failing to provide long-term protection.

TABLE 16

Destruction of OATD Sunscreen by UV Radiation Intensity of 315 J/cm$^2$

|  | OATD-SMC sunscreen | SMC + OATD sunscreen | TiO$_2$ + OATD sunscreen | OATD sunscreen |
|---|---|---|---|---|
| Original SPF | 30.04 ± 0.97 | 25.69 ± 0.51 | 26.07 ± 0.99 | 30.16 ± 0.76 |
| 315 J/cm2 Destructing SPF | 23.84 ± 0.77 | 19.05 ± 1.01 | 18.79 ± 0.81 | 18.22 ± 1.15 |
| Degradation percentage | 20.64% | 25.85% | 27.92% | 39.59% |
| Original Abs$_{360}$ | 1.158 | 1.001 | 0.893 | 1.220 |
| Abs$_{360}$ after 315 J/cm2 | 0.829 | 0.591 | 0.527 | 0.592 |
| Degradation percentage | 28.41% | 40.96% | 40.99% | 51.48% |

The silica microcapsule formed by the sol-gel technique can provide sun protection similar to that provided by physical UV filters. When used together with chemical UV filters, the required amount of chemical UV filters can be reduced. The chemical UV filters can be entrapped by the silica microcapsules to avoid photodegradation and phototoxicity while reducing the risk of allergic reaction by avoiding direct contact with the skin.

Although specific embodiments have been illustrated and described, numerous modifications and variations are still possible without departing from the scope of the invention. The scope of the invention is limited by the accompanying claims.

The invention claimed is:

1. A method for producing microcapsules with a sun protection effect, comprising:
    hydrolysis and condensation: mixing tetraethoxysilane (TEOS), ethanol, and water and uniformly vibrating the mixture of TEOS, ethanol, and water, with the TEOS, ethanol, and water;

adding nitric acid to adjust the mixture of TEOS, ethanol, and water;
placing the mixture still to hydrolyze the mixture;
heating and stirring the hydrolyzed mixture to obtain a TEOS sol; and
microemulsion polymerization: mixing the TEOS sol with Span 80, and mineral oil to obtain a microemulsified TEOS gel;
centrifuging the microemulsified TEOS gel;
removing the oil phase;
sucking and filtering the remaining water phase to obtain a powder;
cleaning the powder with organic solvent; and
baking the powder in an oven.

2. The method as claimed in claim 1, wherein the ratio of TEOS, ethanol, and water is 1:1-5:2-10.

3. The method as claimed in claim 1, wherein the pH value of the mixture of TEOS, ethanol, and water is 0-4 after the addition of nitric acid.

4. The method as claimed in claim 1, wherein in the hydrolysis and condensation, vibration is carried out for 5-40 minutes using supersonic waves, the heating temperature is 50-95° C., the stirring speed is 500-3000 rpm, and the stirring time is 20-120 minutes.

5. The method as claimed in claim 1, wherein the ratio between TEOS sol, Span 80, and mineral oil is 1:0.5-4:1-10.

6. The method as claimed in claim 1, wherein in the microemulsion polymerization, the heating temperature is 50-95° C., the stirring speed is 500-3000 rpm, the stirring time is 20-120 minutes, the centrifuging speed is 3000-7000 rpm, the centrifuging time is 10-50 minutes, the oven temperature is 35-80° C., and the baking time is 8-36 hours.

7. The method as claimed in claim 1, wherein the hydrolysis and condensation further comprises adding a UV filter, wherein the UV filter, TEOS, and ethanol are combined before mixing with water.

8. The method as claimed in claim 7, wherein the ratio between the UV filter, TEOS, and ethanol is 1:0.5-4:1-10.

9. The method as claimed in claim 8, wherein the pH value is 0-4 after the addition of nitric acid.

* * * * *